(12) United States Patent
Ivanov

(10) Patent No.: US 8,471,224 B2
(45) Date of Patent: Jun. 25, 2013

(54) METHOD FOR DETERMINING PATHS OF PARTICLE BEAMS THROUGH 3D TISSUE VOLUMES

(75) Inventor: Yuri Ivanov, Arlington, MA (US)

(73) Assignee: Mitsubishi Electric Research Laboratories, Inc., Cambridge, MA (US)

( * ) Notice: Subject to any disclaimer, the term of this patent is extended or adjusted under 35 U.S.C. 154(b) by 213 days.

(21) Appl. No.: 12/779,641

(22) Filed: May 13, 2010

(65) Prior Publication Data

US 2011/0280372 A1 Nov. 17, 2011

(51) Int. Cl.
*A61N 5/10* (2006.01)

(52) U.S. Cl.
USPC .......................................... 250/492.1; 378/65

(58) Field of Classification Search
USPC ........ 250/492.1, 492.3, 396 R, 307, 396 ML, 250/400; 378/65
See application file for complete search history.

(56) References Cited

U.S. PATENT DOCUMENTS

| | | | | |
|---|---|---|---|---|
| 7,507,977 | B2 * | 3/2009 | Weiguo et al. | 250/492.1 |
| 7,616,735 | B2 * | 11/2009 | Maciunas et al. | 378/69 |
| 2007/0286343 | A1 * | 12/2007 | Maciunas et al. | 378/65 |
| 2010/0072365 | A1 * | 3/2010 | Shoham et al. | 250/307 |
| 2010/0072389 | A1 * | 3/2010 | Tachikawa et al. | 250/396 R |
| 2010/0117002 | A1 * | 5/2010 | Rinecker et al. | 250/396 R |
| 2010/0163727 | A1 * | 7/2010 | Bell et al. | 250/307 |
| 2010/0243911 | A1 * | 9/2010 | Fujii et al. | 250/400 |
| 2012/0001085 | A1 * | 1/2012 | Fujimoto et al. | 250/396 ML |
| 2012/0293514 | A1 * | 11/2012 | Virtue et al. | 345/424 |

FOREIGN PATENT DOCUMENTS

EP 2177244 4/2010

OTHER PUBLICATIONS

Chu W et al. "Instrumentation for Treatment of Cancer Using Proton and Light-Ion Beams," Review of Scientific Instruments, AIP, Melville, NY US vol. 64, No. 8, Aug. 1, 1993, pp. 2055-2122.

* cited by examiner

*Primary Examiner* — Davis A Vanore
*Assistant Examiner* — Wyatt Stoffa
(74) *Attorney, Agent, or Firm* — Gene Vinokur; Dirk Brinkman

(57) ABSTRACT

A path of a particle beam is determined through a 3D planning treatment volume (PTV), wherein the PTV includes a set of slices in a depth order, and each slice includes a set of locations. For each slice, the set of locations are grouped into a set of lines along a selected direction, wherein each line is a straight line and includes a starting location and an ending location, and each line is connected to one or two other lines, and the connecting connects two lines to either the starting location or the ending location of the lines to form a tour, and the tours are connected through the slices in the depth order to form the path of the particle beam.

6 Claims, 17 Drawing Sheets

Method 1: Volume path construction: $P \leftarrow$ MakeVolumePath

Input: A planning treatment volume (PTV) stop locations $V(x, y, z)$
Output: Volume traversal path $P$
   {The $P$ traverses the volume $V$ such that each locations is traversed once}
1: Partition $V$ into $N_z$ planar slices $\{S\}_z$ for every unique value of $z$
2: $N_z \leftarrow \|\{S\}_z\|$
3: for every slice $s$ in $\{S\}_z$ do:
4:    $P_z \leftarrow$ MakePath($s$)
5: end for
   {Merge all planar paths}
6: $P \leftarrow P_1$
7: for $z = 2, ..., N_z$ do:
8:    $P \leftarrow$ MergePaths($P_1$, $P_z$)
9: end for
10: return $P$

*Fig. 1C*

Method 2: Planar path construction: $P \leftarrow$ MakePlanarPath($S$)

Input: A planar array of locations on the grid $S(x, y)$
Output: Planar path $P$ {Construct a path $P$ that spans the planar slice $S$}
{Partition $S$ into $N_r$ regions $\{R\}_n$ such that every $R_n$ is X-convex.}

1: $\{R\}_n \leftarrow$ ConvexPartition($S$)
2: $N_r \leftarrow \|\{R\}_n\|$
3: for every $r$ in $\{R\}n$
4:     $P_n \leftarrow$ MakeXConvexPath($r$)
5: end for
    {Merge all partial solution paths}
6: $P \leftarrow P_1$
7: for $n = 2, ..., N$ do
8:     $P \leftarrow$ MergePaths($P_1, P_n$)
9: end for
10: return $P$

*Fig. 2*

Method 3: Convex partitioning: $\{R\}_n \leftarrow$ ConvexPartition($S$)

Input: A set of planar array of locations on the slice $\underline{S}(x, y)$.
Output: Set of convex regions $\{R\}_n$.
{Partition $S$ into a set of regions $\{R\}_n$, such that every $R_n$ is $X$-convex.}

1: $\{L\}_n$ RasterizeSlice($S$).
   {Gather lines into regions}
2: $\{R\} \leftarrow \{\emptyset\}$
3: $k \leftarrow 1$
4: repeat
5:   $M$ = PercolateDown($\{L\}_n, L_1$)
6:   $R_k$ = GetMarked($\{L\}_n, M$)
7:   $\{L\}_n$ = RemoveMarked($\{L\}_n, M$)
8:   $k \leftarrow k + 1$
9: until $\|\{L\}_n\| = 0$
10: return $\{R\}_n$

*Fig. 3A*

Method 4: Convex path construction: $T_n \leftarrow$ MakeXConvexPath($r$)

Input: A convex planar raster array of lines $r$
Output: Path $P_n$,
{Construct a path $P_n$ that spans the X-convex raster set $r$}

1: $S \leftarrow \emptyset$ {Sweep}
2: $B \leftarrow \emptyset$ {Base}
3: $R \leftarrow \emptyset$ {Return}
4: $Nl \leftarrow \| \{r\} \|$ {Count number of lines in $r$}
{Construct Return path}
5: for every $l$ in $\{r\}$ do
6:     Push($R$, $l[1]$)
7:     $l[0] \leftarrow \emptyset$
8: end for
{Construct Sweep path}
9: for $n = 1, ..., (2\lfloor N_{l/2} \rfloor - 1)$ do
10:     if $n$ is Odd then
11:         PushEach($S$, $r[n]$))
12:     else
13:         PushEach($S$, Reverse($r[n]$))
14:     end if
15: end for
{construct Base path}
16: if $N_l$ is Even then
17:     $B \leftarrow$ Reverse($r[M]$)
18: else
19:     $B \leftarrow$ MakeZipperBase($r[(N_l - 1)...N_l]$)
20: end if
{Merge paths}
21: return $P_n \leftarrow$ Concatenate($S$, $B$, $R$)

*Fig. 4B*

Method 5, Zipper Base Construction: B ← MakeZipperBase(r)

Input: A two-line raster r.
Output: Zipper base B covering raster r.
{Construct a zipper base B covering the two-line raster raster r.}

1: $[P1, P2, P3]$ ← SplitBase($r[1], r[2]$)
2: if Overhang($P1$) then
3:    $O$ ← MakeOpeningType_I($P1$)
4: else
5:    $[O, P2]$ ← MakeOpeningType_II($P1, P2$) {Two rightmost sites of $P2$ moved to $P1$.}
6: end if
7: if Overhang($P3$) then
8:    $C$ ← MakeClosingType_I($P3$)
9: else
10:    $[C, P2]$ ← MakeClosingType_II($P3, P2$) {Two leftmost sites of $P2$ moved to $P3$.}
11: end if
12: $Z$ ← Zipper($P2$) {Remaining sites of $P2$ alternated to a zipper.}
13: return $B$ ← Concatenate($O, Z, C$)
{Merge paths}

*Fig. 5*

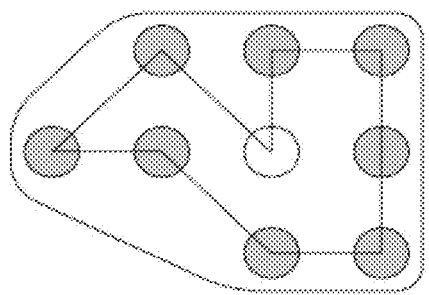
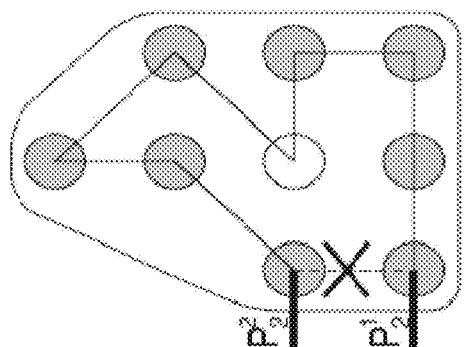
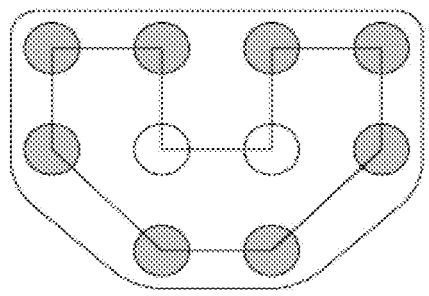
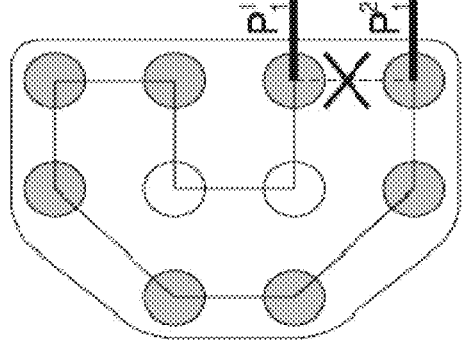
Fig. 6
Fig. 7

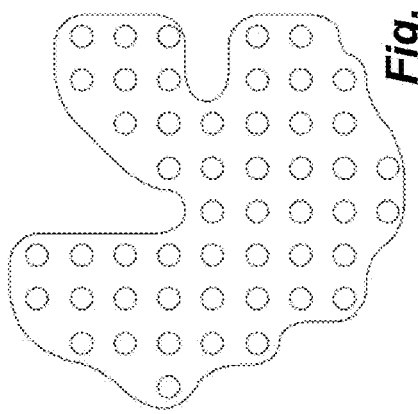
Fig. 10A slice
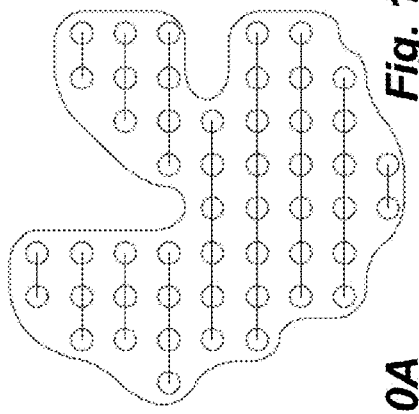
Fig. 10B raster scan
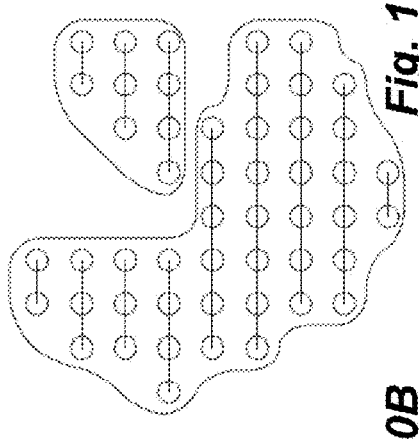
Fig. 10C convex regions
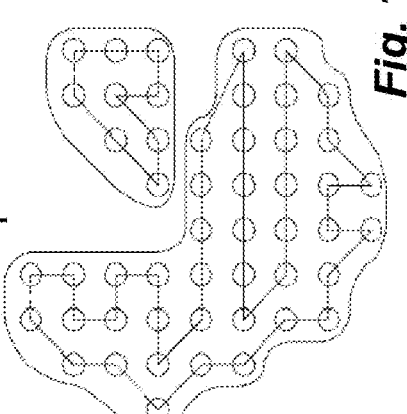
Fig. 10D subpaths
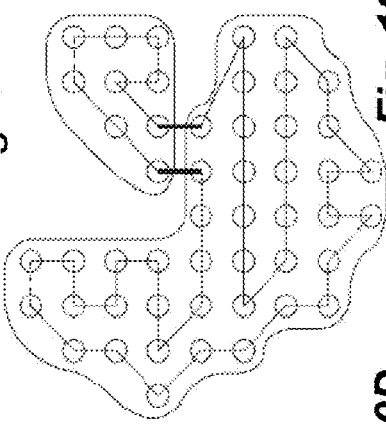
Fig. 10E bridges
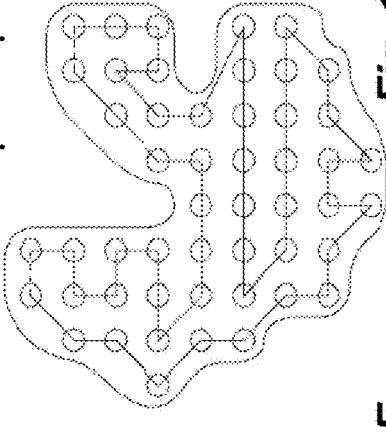
Fig. 10F complete path

METHOD FOR DETERMINING PATHS OF PARTICLE BEAMS THROUGH 3D TISSUE VOLUMES

FIELD OF THE INVENTION

This invention relates generally treatment planning for radiation therapy, and more particularly to determining a path of an ionized particle beam through a 3D tissue volume.

BACKGROUND OF THE INVENTION

In particle beam therapy, one problem is to determine a path for the beam that takes the least amount of time, and delivers the prescribed dose. The problem is formulated as follows. Given a 3D planning target volume (PTV), discretized to a large number of 3D locations in the volume where the beam stops to deliver the dose, a path planner needs to find the path through the beam-stop locations, such that each location is traversed only once. Each location represents an approximate small cube ($mm^3$) in a volume of tissue The 3D locations that are traversed by the ionized beam can be controlled horizontally by magnets arranged in the XY plane, and vertically by adjusting energy in the Z direction (depth). Due to physical constraints of the treatment equipment, change of the beam depth is relatively slow. Hence movement of the beam in the XY plane is preferred. Utilizing this observation, most conventional methods for path optimization reduce the complexity of the optimization task by treating each discrete slice of beam-stop locations independently of others, and only consider a set of 2D solutions, i.e., one per slice. This reduces the computational complexity of the task.

However, even slice-by-slice exact solution in a direct formulation for any realistic size of the problem (~5,000-40,000 locations per slice) cannot be obtained in reasonable time. Several conventional methods determine the path for the beam using a well known traveling salesman problem (TSP). For example, some methods using a path planner that approximates the optimal path for the TSP problem. On the other hand, approximate solutions to the direct TSP formulation using a conventional TSP solver have the following disadvantages.

High Computational Complexity

The exact solution to the TSP has a complexity of $O(n!)$. Thus, a realistic problem of several thousand locations takes a prohibitive amount of time. Approximate solutions can be obtained in polynomial time, which still can be unacceptably long.

Difficulty in Enforcing Path Constraints

The constraints in conventional traditional TSP solvers are usually expressed as a process of distance computation. The edge cost is determined such that every pair of nodes has some associated cost. Unfortunately, a path self-intersection constraint, important in radiation therapy, cannot be expressed using only pairs of nodes.

Accordingly, it is desired to reduce amount of computational time spend on determining the path of the particle beam through a 3D tissue volume.

SUMMARY OF THE INVENTION

Considering the problem from the point of view of an actual treatment enables us to formulate path heuristics, which are typically difficult to enforce in the conventional TSP solver. Our path heuristics enable an ultra-fast acceptable solution.

The invention is based on a realization that there is no reason to find an optimal path connecting all locations in the slice, because the particle beam moves faster along only a selected direction, i.e., the X direction. Thus, the locations are grouped along that fast direction. Then, we find a path connecting all lines. Because we connect lines, instead of locations as in the prior art, our method is much faster than conventional methods.

The method is purely in the form of a "construction." Optimization is not performed at any step, so the method works as fast as the covering path can be constructed, regardless of the implied search time in the space of all possible paths.

The method partitions each slice of the generally complex treatment planning volume (TPV) into a set of smaller regions for which a path is constructed. Then the paths covering each region are merged to construct a continuous path through all regions.

The slice is partitioned into a set of areas convexed into the fast (X) direction. This partitioning is based on a second realization, that for X-convex areas, lines are easily connected to into the paths. Each area is traversed using a tour, which includes a starting location, the path and a return to the starting location. The construction of the tour is based on a third realization that the tours of different areas can be connected using any two neighboring points of each tour. Thus, after having tours, we connect the tourse using the two neighboring locations of each tour.

Alternatively, the connection between the lines can be optimized. However, the main importance, is that optimization is done for lines, not for individual locations as in the prior art.

The features that make this construction possible, valid, and fast are listed below.

Depth Partitioning.

Changing the treatment depth is a relatively slow process due to the necessity of changing the energy of the particle beam. Thus, the full problem of a 3D volume traversal can be reduced to a set of independent slice traversals.

Horizontal Scan Preference

In the scanning particle beam machines, it is often the case that movement of the beam along a horizontal direction is faster than the vertical direction. Thus, horizontal movement of the particle beam is preferred.

Volume Partitioning

Complex slices are partitioned into regions. Taking into account the previous location, convex partitioning is not strictly necessary, because the X direction is faster, it is preferred to the Y direction. Thus, the regions only need to be convex in the X direction, as described below.

Path Solutions

As described below, a key strategy of the method is to determine a set of tours as an intermediate solution to each of the problems. Merging two tours results in a valid path, and therefore can be used for subsequent merges.

BRIEF DESCRIPTION OF THE DRAWINGS

FIG. 1C is pseudo code of a method for constructing a volume path according to embodiments of the invention;

FIG. 2 is pseudo code of a method for constructing a planar path according to embodiments of the invention;

FIG. 3A is pseudo code of a method for partitioning a slice into X-convex regions according to embodiments of the invention;

FIG. 4B is pseudo code of a method for convex path construction according to embodiments of the invention;

FIG. 5 is pseudo code of a method zipper base construction according to embodiments of the invention;

FIGS. 6 and 7 are schematics of bridging for tour construction according to embodiments of the invention;

FIGS. 10A-10F are schematics of a method for constructing a complete path according to embodiments of the invention.

DETAILED DESCRIPTION OF THE PREFERRED EMBODIMENTS

Figure 1A:
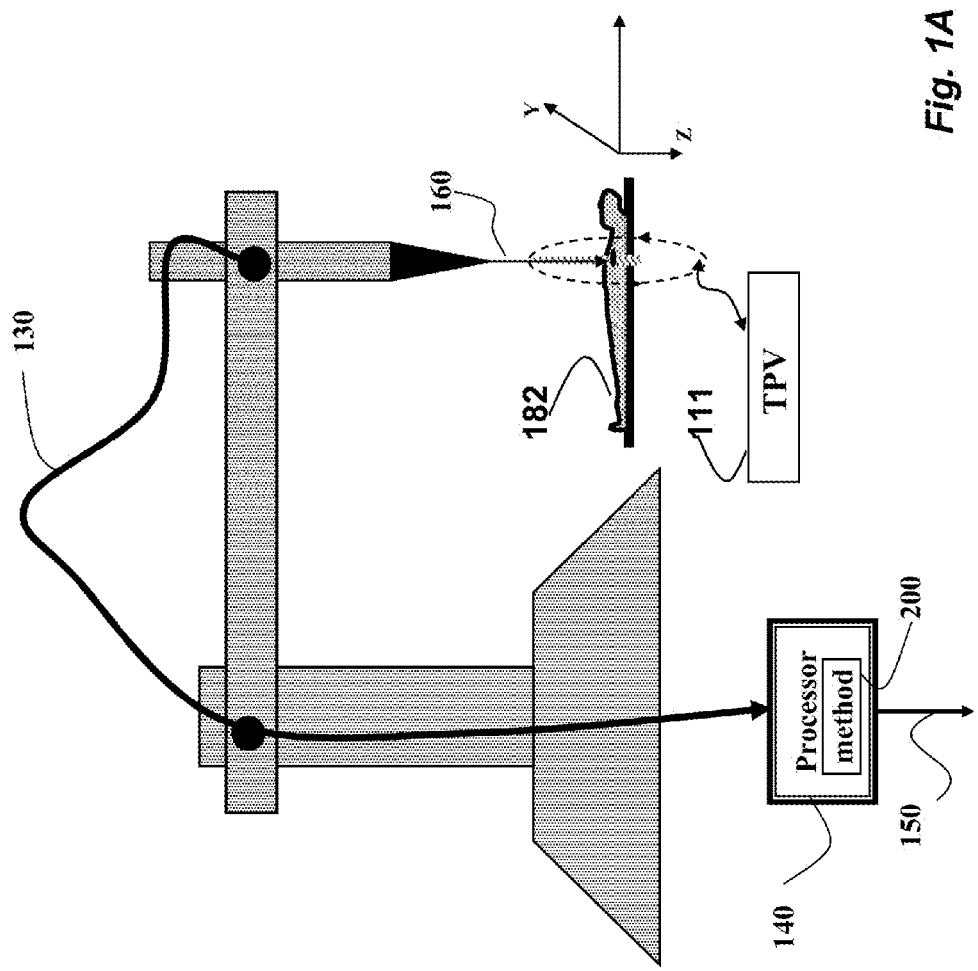
FIG. 1A is a schematic of a system 100 and a method for determining a path of a radiotherapy particle beam through a 3D treatment planning volume.

FIG. 1A shows a system and a method 200 for determining a path 150 of a radiotherapy particle beam 160 through a 3D treatment planning volume (TPV) 111, e.g., tissue of a patient 182. However, embodiments of the invention determine a path through any type of 3D and/or 2D volumes. The method 200 is executed by a processor 140 as known in the art. The TPV is partitioned into a set of slices. The slices are substantially coplanar. In practice, the slices are aligned according to the iso-energies of the beam.

Figure 1B:
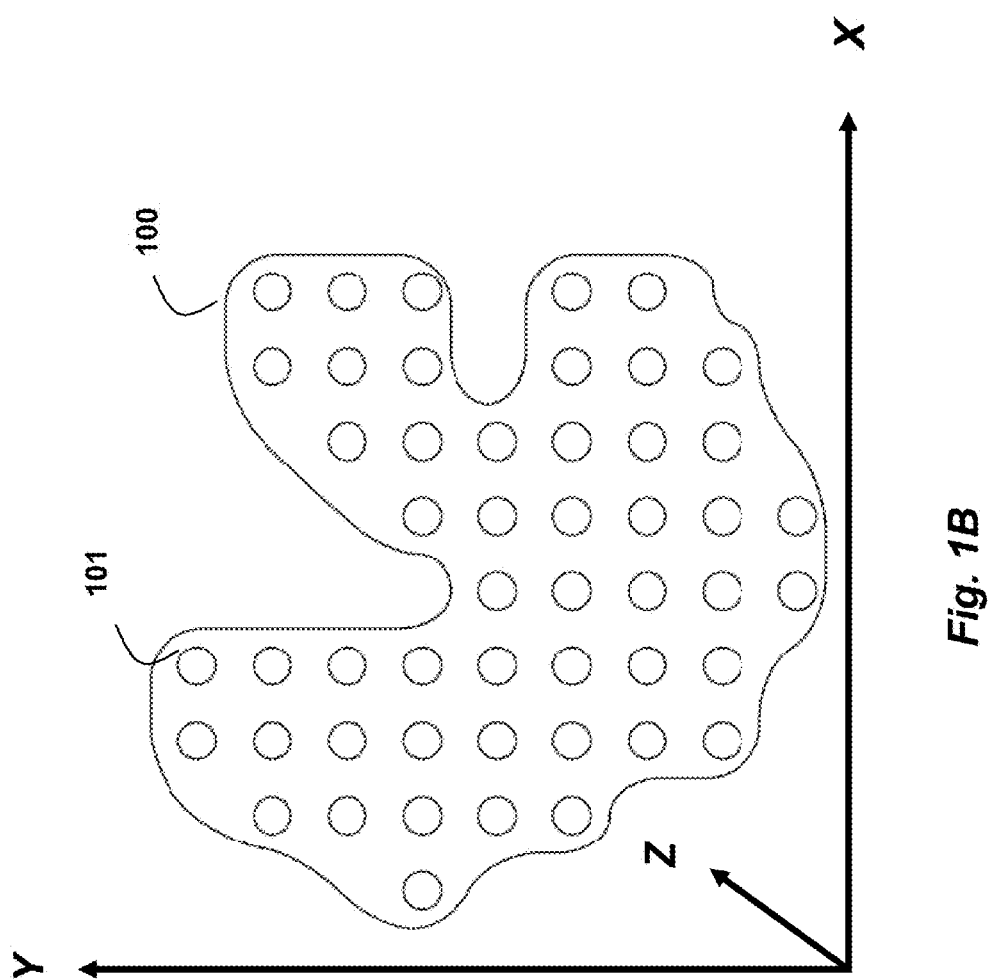
FIG. 1B is a schematic of slice of a planning treatment volume and locations according to embodiments of the invention.

FIG. 1B shows one such slice 100 that is substantially orthogonal to the beam. That, is the slices are in the mostly XY (planar) direction, and the beam is in a Z (depth) order. Herein, the notation {.} designates sets.

The embodiments of the invention are based on a realization that, for any slice, the particle beam moves faster in one direction, i.e., the selected direction, then in another. Accordingly, the embodiments of the invention acquire the selected direction, group the locations of the in the lines along the selected direction, and connect the lines to form a path through the slice as described in more details below.

For example, in one embodiment, the selected direction is predetermined, in another embodiment the selected direction is received during an initialization stage. One embodiment stores a lookup table having different type of particle beams associated with the selected direction etc.

Each slice includes a set of locations 101 arranged in a grid where the beam stops to deliver a radiation dose. In actual practice, the locations are approximately spatially contiguous ($mm^3$) cubes of tissue.

A tour is determined independently for each slice, see FIGS. 10A-10F.

Then, the intra-slice tours are merged. Hence, the method is described for one slice. Then, using the set of paths for the individual slices, the same intra-slice path merging approach can be used to connect the intra-slices tours into a single complete path of the beam moving through the entire TPV.

Volume Path Construction

FIG. 1C shows the pseudo code for the Method 1 for volume path construction. The method takes the volume of predetermined treatment locations arranged in a 3D volume V, and, as a first step, partitions the volume V into a set of slices in XY planes. As stated above, the slices generally follow the contour of iso-energies. The Z direction is used for the initial partitioning. The Z direction is along the direction of the beam.

In current practical applications, changing the energy of the beam is significantly slower than deflecting the beam with magnets arranged in the XY plane. Thus, a change of beam position along the Z-direction induces a largest amount of time of transitions between treatment locations.

This observation enables us to dramatically reduce the computational complexity of the full problem of finding the path in the volume to finding a set of paths in each slice independently from one another.

At the next step, the method constructs a set of paths, one for each substantially planar slice, by calling the MakePath function, described below.

The paths for all slices are merged into a single path. For simplicity of this description, the method assumes that the slice solutions are arranged in some selected depth order of z. Thus, merging of the slice solutions into the global solution for the volume can proceed in this order.

Plane Path Construction

FIG. 2 shows the pseudo code for the Method 2 of plane path construction. The method makes repeated calls for independent plane path construction by calling MakePlanarPath. The operation of MakePlanarPath is similar to that of MakeVolumePath.

The initial partitioning of the region is followed by constructing paths in each region, and merging of all paths into one path, which is returned by the method.

Partitioning

Figure 3D:
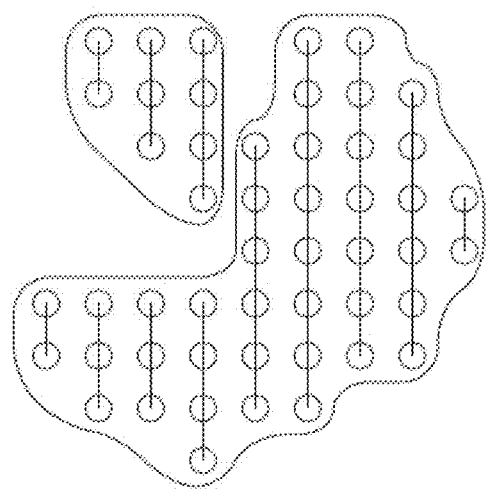
FIGS. 3B-3D are schematics of the partitioning according to embodiments of the invention.
Figure 3C:
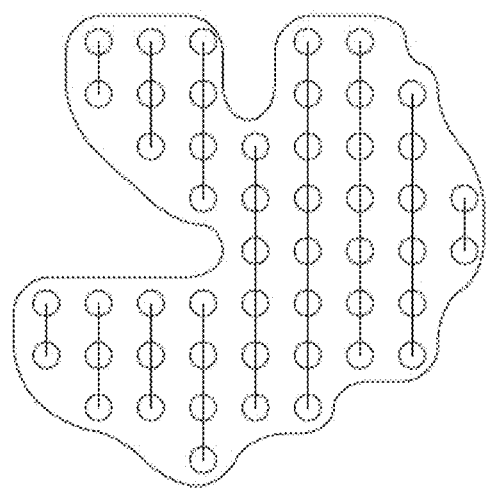
Figure 3B:
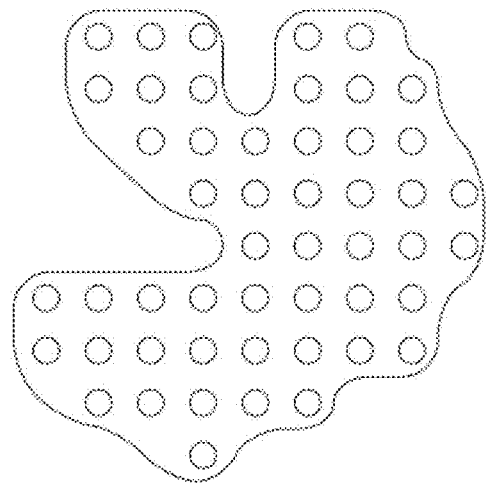

The steps for partitioning of the generally complex disjointed and non-convex slice are shown in the pseudo code of Method 3 of FIG. 3A, and schematically in FIGS. 3B-3D. This part of the method partitions the volume into a set of convex regions, each of which is used by the subsequent construction step.

Because movement in the X direction is faster, the X preferred over the Y direction, the regions only need to be convex in the X direction for convex, or monotone partitioning. In monotone partitioning as shown in the figures, any horizontal line has no more than two intersections with the boundary of each partition. As described herein, the method can easily handle regions that are convex in the X-direction. Thus, the partitioning has a goal of reducing the initial volume to a set of X-convex (or convex) regions.

The Method 3 is shown in FIGS. 3B-3D. Input to the Method 3 is shown in FIG. 3B is a planar set of treatment locations arranged in a regular grid. First, the locations are grouped in raster scan lines (rows) by considering neighborhood relations between the locations, as shown in FIG. 3C. If the next location has the same Y value as the previous location, and the X value is X=X+dX for the previous location added to the line, then the next location is also added to the line, where dX is a predetermined (small) distance between treatment locations. Otherwise, the location is added as a starting location of a new line to enforce line continuity. After this rasterization step is completed, the region is now converted to a set of lines or rows of locations, as shown in FIG. 3C.

Finally, in several passes, the lines are grouped into regions, such that all regions are contiguous and convex in the X direction. This is achieved by the repeat block of the Method 3. Starting with the first line (k=1), the $k^{th}$ line ($L_k$) of the set of lines ($\{L\}_n$) is considered. Then, a line in the set $\{L\}_n$ with the Y value of Y+dY is located and examined for overlap with line $L_1$. If the set overlaps, then the set is marked as belonging to the current region. The index k is increased, and the process is repeated until no more candidate lines are found to continue the region.

In the next step all marked lines are moved from the set $\{L\}_n$ into $R_i$. Subsequently, the search is repeated from line $L_1$ in the set of the remaining lines to construct the next region, until no more lines remain in the set $\{L\}_n$. The method produces a set of X-convex regions as shown in FIG. 3D.

Line Stacking

Figure 4A:
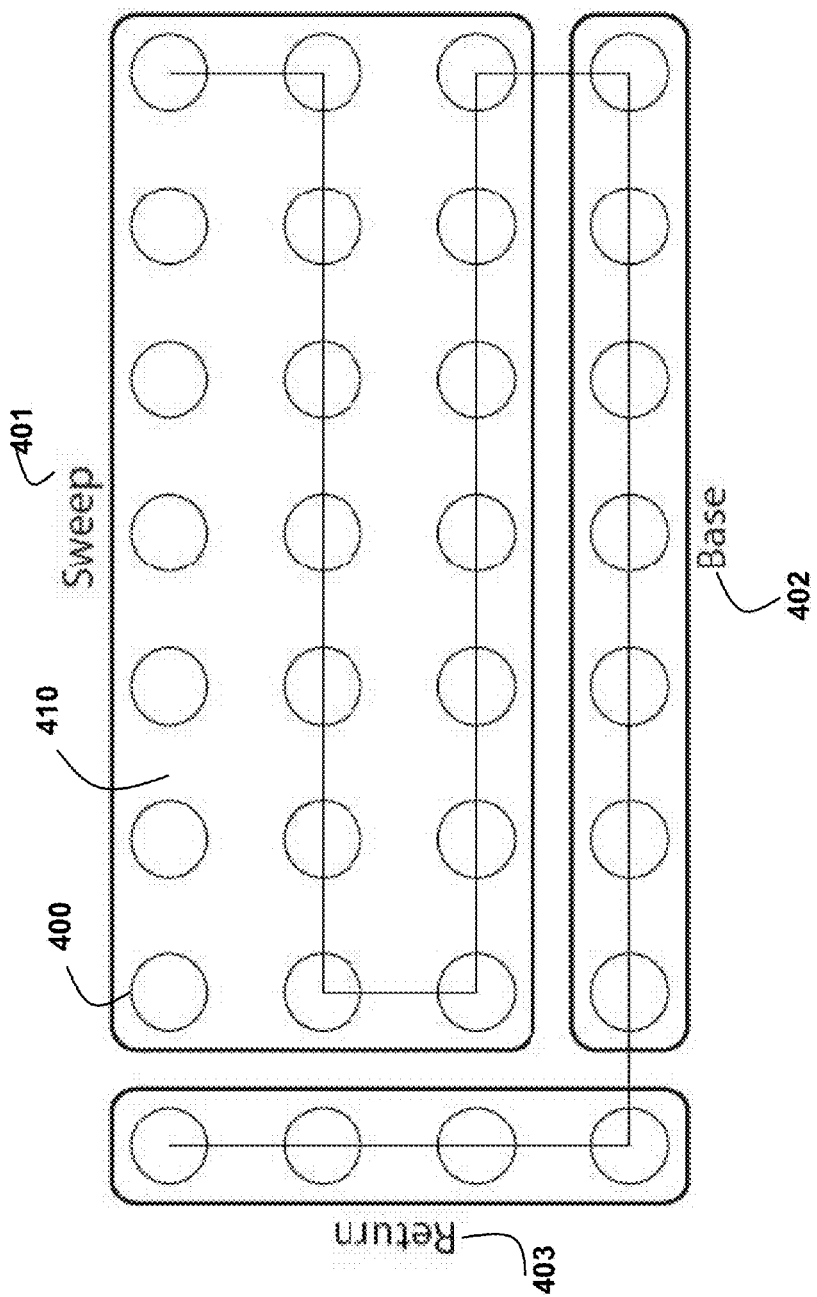
FIG. 4A is a schematic of line stacking according to embodiments of the invention.

Line stacking is shown in FIG. 4A. Beginning at a starting location 400, a subpath 410 passes through a sweep area 401, then a base area 402, and then a return area 403, each of which is constructed differently. The line stacking is implemented in Method 4 MakeXConvexPath shown in FIG. 4B. The method uses several heuristics that allow the construction of an efficient path out of a collection of locations on lines gathered into a region $R_i$.

The general structure of a raster tour is shown in FIG. 4A. As the figure shows, the tour includes a "lawn-mower" raster sweep beginning at the starting location, followed by the tour base, and a tour return that brings the beam to the starting location 400. Each of these components is constructed differently. A generally clockwise traversal convention is used. That is, a tour starts at the top row, and begins left-to-right. Selecting a particular convention for a tour direction simplifies the tour merging strategy, described below. Of course, the direction can be generally counterclockwise.

Return: The return is the simplest part of the tour. We define the return path as a set of left-most locations in the region. Using the clock-wise traversal convention, the return is always directed from the bottom to the top.

Sweep: Again, using the clockwise traversal convention, the sweep always contains an odd number of rows. The sweep is constructed by traversing every odd line left-to-right, and every even line right-to-left. Thus, every last location of every odd line is adjacent to the last location of the following even line, and every second location of every even line is adjacent to the second location of the following odd one. This implies that the direction of the last line is left-to-right, and the bottom right location of the sweep region is the exit location.

Base: The base requires some care in its construction. The base has the remaining locations between the sweep and return areas. Because the sweep always contains an odd number of rows, the base can have either one or two rows. The base of one row is simply traversed right-to-left.

Figure 4C:
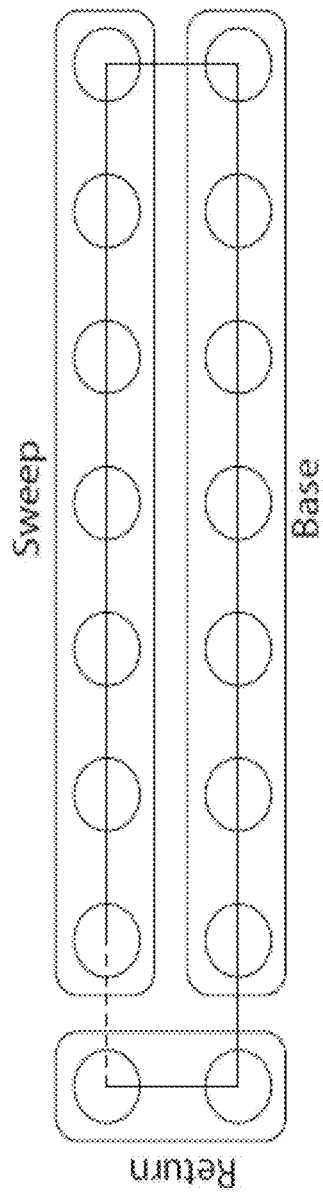
FIG. 4C is a schematic of an even tour according to embodiments of the invention.

FIG. 4C shows an even tour. The sweep formed by the first line connects to a single-line base, which returns to the first location of the top line. In contrast, adding a line to the region leads to a more complicated odd tour. The problem is that to connect to the return path, the base needs to move the beam from right to left spanning two lines.

Figure 4D:
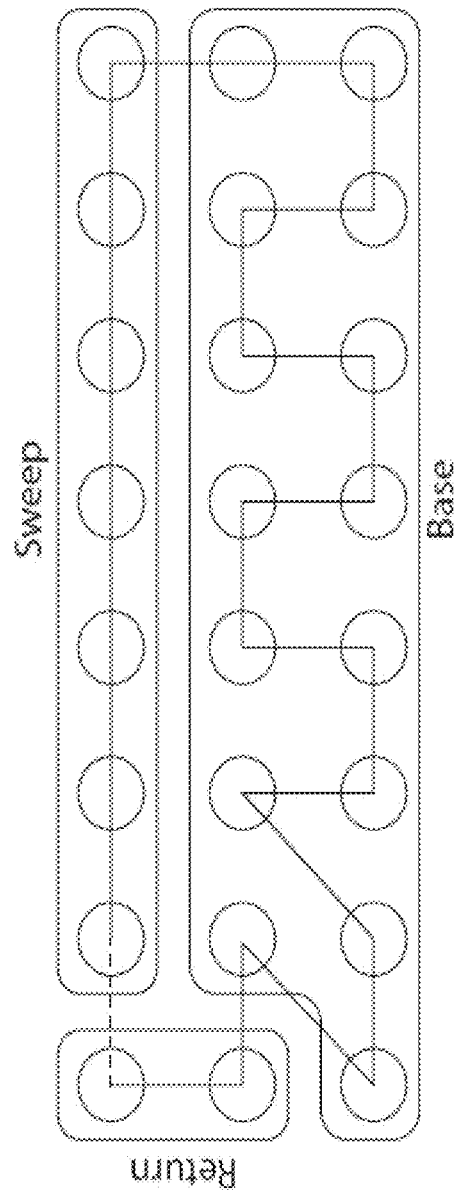
FIG. 4D is a schematic of an odd tour according to embodiments of the invention.
Figure 4E:
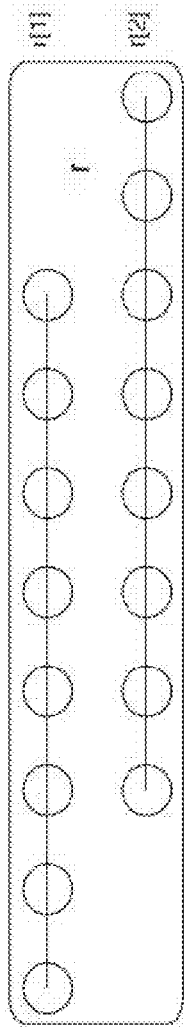
FIGS. 4E-4H are schematics of zipper construction according to embodiments of the invention.

FIG. 4D shows an example of an odd tour. The base of the tour is constructed by a meandering right-to-left traversal of two rows. The base path is constructed by forming a "zipper," which requires two lines.

Zipper Construction

Given a general structure of a base, i.e., a completed zipper base is shown in FIGS. 4E-4H. The base is decomposed into the canonical zipper, and two parts that join the canonical zipper to the rest of the tour by implementing an entry path into the zipper and an exit path out of it. Due to this construction strategy, the base is traversed from right to left, the right-most locations are called an opening, while the left-most locations are called a closing.

Figure 4F:
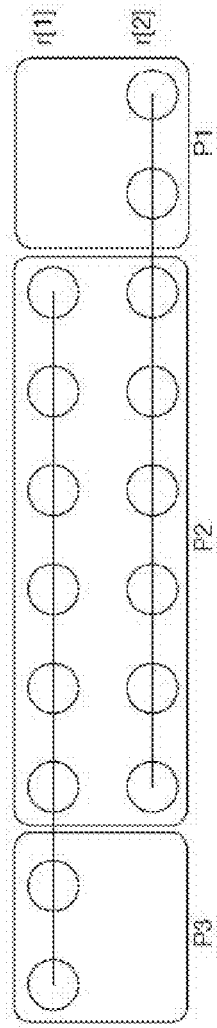
Figure 4G:
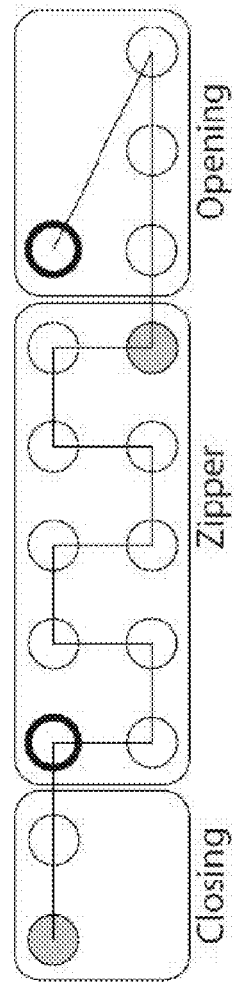
Figure 4H:
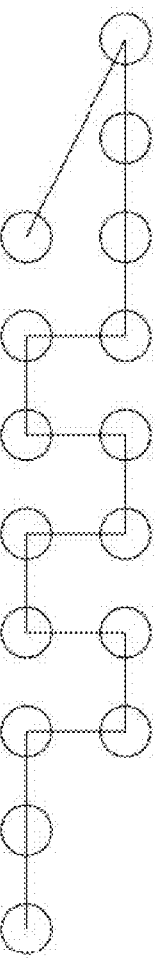
Figures 4I, 4J, 4K, 4L:
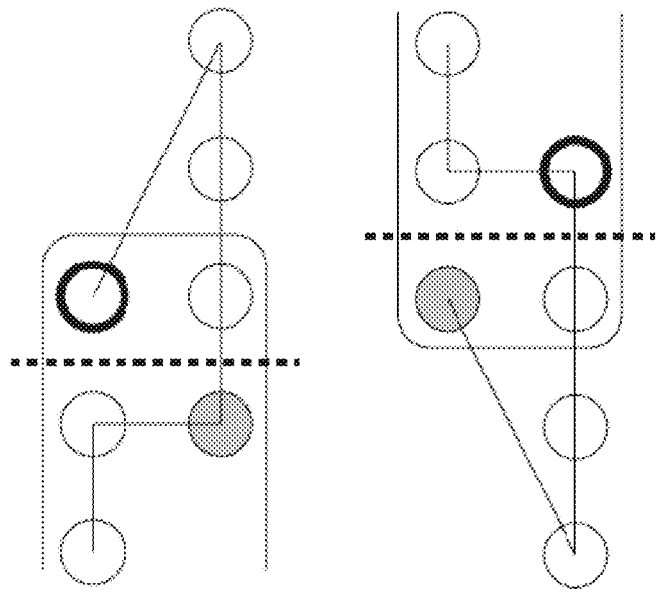
FIGS. 4I-4L are schematics of Type I and Type II opening and closing moves according to embodiments of the invention.

The canonical zipper shape is shown in the center of the FIG. 4F. In the conventional base traversal direction, the shape starts on the bottom line of the region. The ending of the canonical zipper depends on number of columns and can result in a diagonal move between the end of the zipper and the closing move.

To identify the zipper path, the method first identifies the overlapping part of the locations on both lines of the zipper base. Generally, this set of locations is the set from which the canonical zipper is constructed. However, some special cases are considered in constructing the zipper.

If the bottom line is longer on the right then the top line of the base, then the two rightmost locations of the zipper set are taken by the opening, as described below. Similarly, if the bottom line of the base is longer on the left, then the top line of the base, the two leftmost locations of the zipper set is taken by closing.

Depending on the geometry of the two lines of the zipper base, opening and closing can both be of one of two types:
(1) Type I opening and closing moves are applied in the case when the top line of the zipper base overhangs the bottom line on the left (Type I closing) or on the right (Type I opening); and
(2) Type II opening and closing moves are applied in the case when the top line of the zipper base does not overhang the bottom line on the left (Type II closing) or on the right (Type II opening).

Examples of opening and closing moves of both types are shown in FIGS. 4I-4L, respectively, Type I zipper opening move, Type II zipper opening move; Type I zipper closing move; Type II zipper closing move. In the Figures, the partial rounded rectangle outlines the canonical zipper, while the dashed line delineates the boundary between opening and closing moves.

Type II moves use part of the zipper to connect to the base entry and exit locations. The locations outlined with heavy strokes are the sources for the move, while shaded locations designate the move destinations. That is, the goal of the opening or the closing move is to connect the source location to the destination location.

FIGS. 4E-4H show a complete zipper base construction, where the top line overhangs the bottom on the left (closing), but not on the right (opening). Therefore, the base is constructed using Type I closing and Type II opening. As any type II move, the opening consumes two rightmost locations of the zipper location set to provide an entry location into the base on the top right.

The pseudo-code of the zipper base construction Method 5 is shown in FIG. 5. Given the base region, (FIG. 4E), the method starts by splitting the two rows r[1] and r[2] into opening, closing, and zipper sets by a call to SplitBase(r[1], r[2]), as shown in FIG. 4F.

This function finds locations in r[1] and r[2] that share their X-coordinate. This set forms the set of locations that are traversed in the pattern of a canonical zipper, P2. The remaining locations to the right of this set form the opening set, P3, while the locations on the left of the zipper set form the closing set, P1. As a consequence of selecting the zipper set both P1 and P3 contain locations from only a single row.

Next, by invoking Overhang(P1), the method identifies the opening type as Type I or Type II. This is done by determining which row is contained in P1. If the set contains only locations from row r[1], then Overhang(P1) returns TRUE and opening Type I is selected. Otherwise, the two rightmost locations of P2 transferred to P1, and the opening Type II is applied.

Similarly, the appropriate type of closing is selected by considering the set P3 and the method proceeds to process the remaining zipper set P2. After all parts are constructed they are simply concatenated into the completed base.

Tour Merging.

After all the regions found by partitioning according to Method 3 are processed by the Method 4, the subpaths of each convex region are merged into a plane path for each slice, and subsequently, the plane paths are merged into a volume path. As stated above, the merging of the plane paths is in the selected z order.

Both merges are performed by different applications of the same basic approach of region merging. Regions in each plane are merged by proximity. The closest regions are merged first, and the volume merge across planes is performed in the natural order in which the planes are arranged, from first to last in the Z (depth) direction. This is as reflected in Methods 2 and 1 by the invocation of the merge procedure.

To connect two tours into one, we join or "bridge" tours at a location of lowest cost. The cost can be defined by a number of constraints, e.g., distance, presence of organ at risk, direction of the connection, etc. To determine such locations, several issues are considered:

(1) Only the locations on the periphery of each region need to be considered as possible locations where the paths will be merged;
(2) Two tours can be easily joined if a link between two consecutive locations on one path is broken and connected to two consecutive locations of the other path;
(3) The new merged region periphery locations include at most two sets of periphery locations of the merged tours; and
(4) The local directionality of the path around the bridge needs to be taken into account so that the two bridge edges do not cross.

Region Bridging

Region bridging is shown in FIGS. 6 and 7. FIG. 6 shows two merging candidate regions, and FIG. 7 shows the completed bridging.

The bridging method first identifies a pair of locations in each region such that the locations are:

a) on the periphery of the region;
b) consecutive in the path; and
c) closest to the corresponding pair of locations in the other region.

To find such pairs, distances between all periphery (shaded) locations of one region and periphery locations of the other region are determined. Then, all distances between consecutive pairs of locations are summed, and the minimal distance is determined. The edges between the locations of the same regions corresponding to the minimal distance $P^1_1$, $P^2_1$, $P^1_2$, and $P^2_2$) are removed, and replaced with cross-region connecting edges, a bridge, as shown in FIG. 7

Figure 8A:
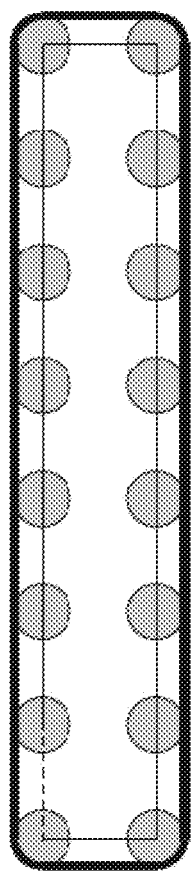
FIGS. 8A-8B are schematics of consecutive and nonconsecutive outline locations in tours according to embodiments of the invention.
Figure 8B:
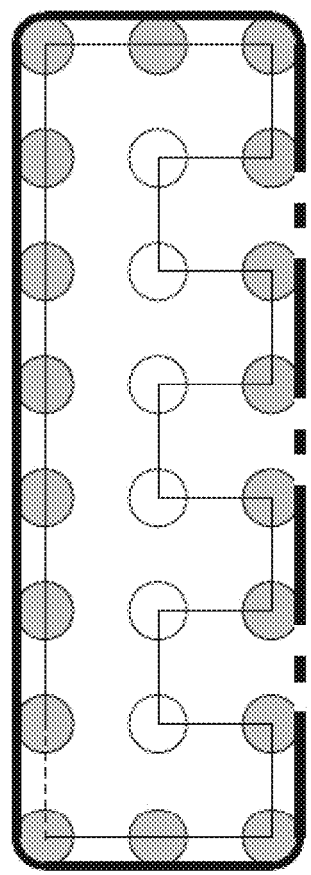

One complicating issue is the possibility that two locations that are consecutive in the outline may not be consecutive in the path. For example, FIGS. 8A and 8B show an even and an odd tours, respectively. The bottom row of the odd path cannot be broken at an arbitrary location because the meander section of the base has locations on the path alternating between the 2nd and 3rd rows, thereby breaking the sequential consistency of the outline. Thus the non-consecutive pairs are identified during the process of determining the region outline, and subsequently removed from consideration. In the illustrations non-consecutive pairs of boundary locations are identified by a dashed outline.

Convex and Non-Convex Merging Strategies

Figure 9A:
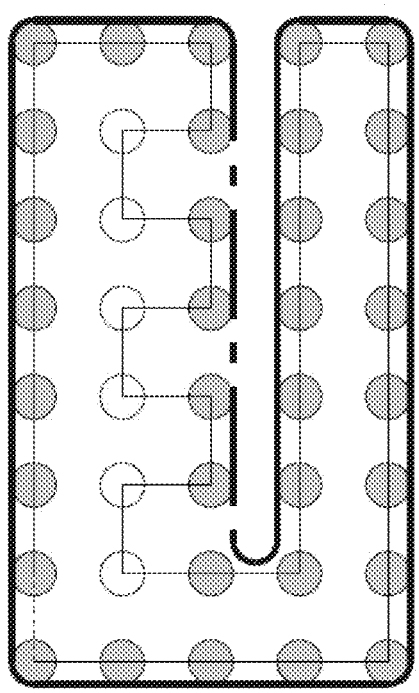
FIGS. 9A-9B are schematics of non-convex and convex path merges according to embodiments of the invention.
Figure 9B:
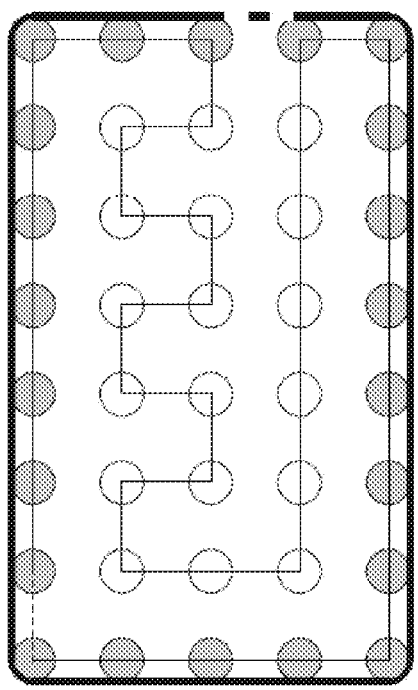

There is an ambiguity about the type of an outline the method maintains during operation. An example of this ambiguity is shown in FIGS. 9A-9B for non-a convex path merge, and a convex path merge. After two paths are merged, the joint outline can include outlines of both regions, as shown in FIG. 9A. This leads to the formation of complicated non-convex joint regions.

Another option is to redetermine the outline, maintaining the monotone convexity property of the original partitioning. This convex strategy works well in practice by reducing the number of calculations required for computing the outline distance matrix. However, in some degenerate circumstances, the solution obtained with this method can result in a complicated bridging pattern. The choice of the strategy can be given as an option to the method, as convex strategy always maintains the periphery set of a region which is compact and fast to determine. In contrast, the non-convex strategy can better accommodate highly partitioned volumes.

Method Summary

A summary of the steps of the method are shown in FIGS. 10A-10F. Starting with the TPV beam locations are identified in each slice of the volume (FIG. 10A). The first step of the method identifies primitive horizontal raster scan lines (or rows of locations) that are subsequently used as traversal units (FIG. 10B).

Using these lines, the method partitions the volume into convex regions, such that each region can be connected by a continuous "lawn mower" path from top to bottom (FIG. 10C.).

For each such region, a tour is constructed so that a traversal direction is conventionally consistent, i.e., generally clockwise in FIG. 10D).

Then a candidate pair of edges in the two paths is identified and the paths are connected by bridging (FIG. 10E).

Figure 11:
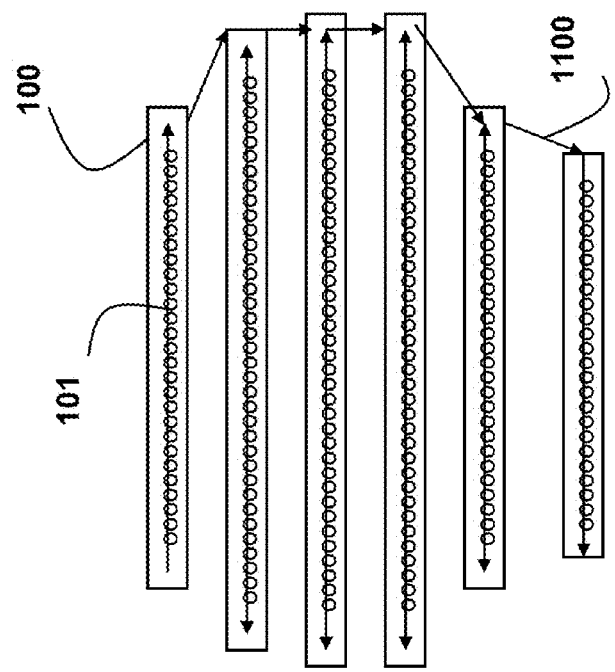
FIG. 11 is a schematic of a global path through the volume.

The complete planar path is shown in (FIG. 10F), and FIG. 11 shows the global 1100 path after the planar paths are merged. Because each layer includes a tour, the layer is fully covered by the paths of the tour, and there is no need to return to the previous layer after the previous layer has been traversed.

Although the invention has been described by way of examples of preferred embodiments, it is to be understood that various other adaptations and modifications may be made within the spirit and scope of the invention. Therefore, it is the object of the appended claims to cover all such variations and modifications as come within the true spirit and scope of the invention.

I claim:

1. A method for determining a path of a particle beam through a 3D planning treatment volume (PTV), wherein the PTV includes a set of slices in a depth order, wherein each slice includes a set of locations, comprising the steps of:

defining X, Y, and Z direction for the particle beam, wherein movement along the X direction is faster than movement along the Y direction, and movement along the Y direction is faster than along the Z direction;

constructing independently tours, wherein the constructing of each tour further comprises:

grouping, for each slice, the set of locations into a set of lines along the X direction, wherein each line is a straight line and includes a starting location and an ending location;

connecting along the Y direction, for each slice, each line to one or two other lines, wherein the two lines are connected to either the starting location or the ending location of the each line, and the ending location is connected to the starting location to form each tour; and connecting the tours through the slices in the Z direction to form the path of the particle beam, wherein the constructed and connected tours minimize a time for the particle beam to traverse the path to deliver a prescribed dose, and wherein the steps are performed in a processor.

2. The method of claim 1, wherein the locations are spatially contiguous cubes of tissue.

3. The method of claim 1, wherein the partitioning of the PTV is planar and in a depth order.

4. The method of claim 1, wherein the lines are constructed independently of each other.

5. The method of claim 1, further comprising:

partitioning each slice monotonically into regions, wherein each region is convex in a selected horizontal direction;

stacking, in each region, the locations in the set of lines into a sweep area including a starting location, a base area, and a return area;

traversing, in each region, the locations in the sweep area, then the base area, and then the return area in a generally clockwise direction beginning and ending at the starting location to construct a sub-path; and merging the subpaths in each region to construct the tour.

6. The method of claim 5, wherein the return area includes left-most location in the region and the traversing is from bottom to top, and the sweep area includes an odd number of rows and the traversing is in left to right in odd lines, and right to left in even lines, and the base includes the remaining locations between the sweep area and the return area.

* * * * *